US007323444B2

(12) United States Patent
Delso

(10) Patent No.: US 7,323,444 B2
(45) Date of Patent: Jan. 29, 2008

(54) USE OF KAHALALIDE COMPOUNDS FOR THE MANUFACTURE OF A MEDICAMENT FOR THE TREATMENT OF PSORIASIS

(75) Inventor: Miguel Angel Izquierdo Delso, Madrid (ES)

(73) Assignee: Pharma Mar, S.A.U., Madrid (ES)

( * ) Notice: Subject to any disclaimer, the term of this patent is extended or adjusted under 35 U.S.C. 154(b) by 0 days.

(21) Appl. No.: 10/546,758

(22) PCT Filed: Feb. 26, 2004

(86) PCT No.: PCT/GB2004/000757

§ 371 (c)(1),
(2), (4) Date: Oct. 10, 2006

(87) PCT Pub. No.: WO2004/075910

PCT Pub. Date: Sep. 10, 2004

(65) Prior Publication Data

US 2007/0032412 A1    Feb. 8, 2007

(30) Foreign Application Priority Data

Feb. 26, 2003    (GB) ............................ 0304367.6

(51) Int. Cl.
*A61K 38/12* (2006.01)
(52) U.S. Cl. .......................... 514/11; 514/9
(58) Field of Classification Search ............... 514/11, 514/544, 9; 530/317, 321
See application file for complete search history.

(56) References Cited

U.S. PATENT DOCUMENTS

| 4,959,175 | A | | 9/1990 | Yatzidis |
| 5,705,511 | A | * | 1/1998 | Hudkins et al. ............ 514/338 |
| 5,849,704 | A | | 12/1998 | Sorensen et al. |
| 5,932,189 | A | | 8/1999 | Dean et al. |
| 6,011,010 | A | * | 1/2000 | Scheuer et al. ............... 514/11 |
| 2003/0157685 | A1 | | 8/2003 | Zervos |
| 2004/0052764 | A1 | | 3/2004 | Hildinger et al. |
| 2004/0067895 | A1 | | 4/2004 | Faircloth et al. |
| 2004/0214755 | A1 | | 10/2004 | Albericio et al. |
| 2005/0054555 | A1 | | 3/2005 | Jimeno et al. |
| 2006/0234920 | A1 | | 10/2006 | Faircloth et al. |

FOREIGN PATENT DOCUMENTS

| EP | 0 610 078 | | 8/1994 |
| EP | 0 838 221 | | 4/1998 |
| WO | WO 99/42125 | | 8/1999 |
| WO | WO 2001/58934 | | 8/2001 |
| WO | WO 2002/36145 | | 5/2002 |
| WO | WO0236145 | A2 * | 5/2002 |
| WO | WO 2003/033012 | | 4/2003 |
| WO | WO 2004/035613 | | 4/2004 |
| WO | WO 2005/023846 | | 3/2005 |
| WO | WO 2005/103072 | | 11/2005 |

OTHER PUBLICATIONS

U.S. Appl. No. 10/182,881, filed Jun. 3, 2003, Fernando Albericio et al.
U.S. Appl. No. 11/587,177, filed Jan. 2, 2007, Andres Francesch Solloso et al.
U.S. Appl. No. 10/492,670, filed Nov. 3, 2004, Jose Jimeno.
U.S. Appl. No. 10/399,571, filed Nov. 14, 2003, Glynn Faircloth.
U.S. Appl. No. 10/642,006, filed Aug. 14, 2003, Paul Scheuer.
U.S. Appl. No. 10/570,734, filed Mar. 6, 2006, Fernando Albericio Palomera et al.
U.S. Appl. No. 10/531,533, filed Apr. 25, 2006, Glynn Faircloth et al.
Vippagunta et al., "Crystalline Solids,"Adv Drug Deliv Rev, vol. 48, iss. 1, pp. 3-26, May 16, 2001.
Nuijen B et al., "Development of a lyophilized parenteral pharmaceutical formulation of the investigational polypeptide marine anticancer agent kahalalide F" Drug Development and Industrial Pharmacy, vol. 27, No. 8, pp. 767-780, 2001.
Faircloth G et al., "Preclinical development of kahalalide F, a new marine compound selected for clinical studies," Proceedings of the American Association for Cancer Research Annual, No. 41, Mar. 2000, pp. 600-601, XP001097542, 91$^{st}$ Annual Meeting of the American Association for Cancer Research, San Francisco CA, USA; Apr. 1-5, 2000, Mar. 2000 ISSN: 0197-016X.
Luber-Narod J et al., "Evaluation of the use of in vitro methodologies as tools for screening new compounds for potential in vivo toxicity." Toxicology In Vitro, vol. 15, No. 4-5, Aug. 2001, pp. 571-577, XP002225749, ISSN: 0887-2333, p. 576, col. 2, paragraph 2.
Brown Alan P et al., "Preclinical toxicity studies of kahalalide F, a new anticancer agent: single and multiple dosing regimens in the rat." Cancer Chemotherapy and Pharmacology. Germany Oct. 2002, vol. 50, No. 4, Oct. 2002, pp. 333-340, XP002225750 ISSN: 0344-5704 abstract.
El Sayed, Khalid A. et al., "The Marine Environment: A Resource for Prototype Antimalarial Agents," Journal of Natural Toxins, vol. 5, No. 2, pp. 261-285, 1996.
Garcia-Rocha, Mar et al., "The antitumoral compound Kahalalide F acts on cell lysosomes," Cancer Letters, vol. 99, No. 1, pp. 43-50, 1996.
Goetz, Gilles et al., "The Absolute Stereochemistry of Kahalalide F," Tetrahedron, vol. 55, pp. 7739-7746, 1999.
Goetz, Gilles et al., "Two Acyclic Kahalalides from the Sacoglossan Mollusk Elysia rufescens," Journal of Natural Products, vol. 60, No. 6, p. 562-567, 1997.
Hamann, Mark T. et al., "Kahalalide F: A Bioactive Depsipeptide from the Sacoglossan Mollusk *Elysia refuscens* and the Green Alga Bryopsis sp.," Journal of the American Chemical Society, vol. 115, No. 13, pp. 5825-5826, 1993.

(Continued)

Primary Examiner—Michael G. Hartley
Assistant Examiner—Jagadishwar Samala
(74) Attorney, Agent, or Firm—King & Spalding, LLP; Kenneth H. Sonnenfeld; Michael A. Willis

(57) ABSTRACT

Kahalalide compounds, in particular kahalalide F, are of use in a method to treat a mammal suffering from skin disease with avoiding toxicity and leading to clinical improvement.

10 Claims, No Drawings

OTHER PUBLICATIONS

Hamann, Mark T. et al., "Kahalalides: Bioactive Peptides from a Marine Mollusk *Elysia refuscens* and Its Algal Diet Bryopsis sp.," The Journal of Organic Chemistry, vol. 61, No. 19, pp. 6594-6600, 1996.

Hamann, Mark T. et al., "Kahalalides: Bioactive Peptides from a Marine Mollusk *Elysia refuscens* and Its Algal Diet Bryopsis sp.," The Journal of Organic Chemistry, vol. 63, No. 14, pp. 4856, 1998.

Horgen, F. David et al., "A New Depsipeptide from the Sacoglossan Mollusk Elysia ornate and the Green Alga Bryopsis Species," Journal of Natural Products, vol. 63, No. 1, pp. 152-154, 2000.

Kan, Yukiko et al., "Kahalalide K: A New Cyclic Depsipeptide from the Hawaiian Green Algo Bryopsis Species," Journal of Natural Products, vol. 62, No. 8, pp. 1169-1172, 1999.

Lopez-Macia, Angel et al., "Kahalalide B. Synthesis of a natural cyclodepsipeptide," Tetrahedron Letters, vol. 41, pp. 9765-9769, 2000.

Goodman & Gilman's, The Pharmacological Basis of Therapeutics, Ninth Edition, McGraw Hill, New York (1996), Section X, Chemotherapy of Neoplastic Diseases, pp. 1225-1229.

Hamann, Mark Todd, Ph.D., University of Hawaii (1992), "Biologically Active Constituents of Some Marine Invertebrates," UMI Dissertation Services, published Oct. 1993.

Merck Manual, 11$^{th}$ ed., pp. 456-459, 761-763, and 1368-1371; published 1969.

Lee Y S et al., "A convergent liquid-phase synthesis of salmon calcitonin" Journal of Peptide Research, Munksgaard International Publishers, Copenhagen DK, vol. 54, No. 5, Oct. 1999, pp. 328-335, XP000849313 ISSN: 1397-002X, figure 1.

Bonnard Isabelle et al., "Stereochemistry of kahalalide F," Journal of Natural Products. Nov. 2003, vol. 66, No. 11, Nov. 2003, pp. 1466-1470, XP002337530 ISSN: 0163-3864 abstract.

Lopez-Macia et al., "Synthesis and Structure Determination of Kahalalide F." J. Am. Chem. Soc., vol. 123, No. 46, pp. 11398-11401, published on web Oct. 27, 2001.

Gura, "Cancer Models-Systems for identifying new drugs are often faulty," Science, vol. 278, pp. 1041-2, Nov. 7, 1997.

\* cited by examiner

USE OF KAHALALIDE COMPOUNDS FOR THE MANUFACTURE OF A MEDICAMENT FOR THE TREATMENT OF PSORIASIS

FIELD OF THE INVENTION

Use of kahalalide compounds for the manufacture of a medicament for the treatment of psoriasis

BACKGROUND OF THE INVENTION

Psoriasis is a chronic, genetically-influenced, remitting and relapsing scaly and inflammatory skin disorder that affects 1 to 3 percent of the world's population. It is characterized by erythematous, sharply demarcated papules and rounded plaques, covered by silvery micaceous scale. The skin lesions of psoriasis are variably pruritic. There are several types of psoriasis, including plaque, pustular, guttate and arthritic variants. There is at present no cure for psoriasis, but rather only suppressive therapy (Greaves and Weinstein, 1995, Drug Therapy, 332: 581-588).

The disease appears at two different ages. The premature disease presentation (type 1), with a peak between 15 and 35 years of age, is the most frequent and is normally associated to family records. The late disease presentation (type 2) is presented in a peak of the ages between the 55 and the 60 years.

It is not known what causes psoriasis, although there is evidence of a genetic predisposition and an autoimmune etiology. Onset may be triggered by systemic infections such as strep throat, skin injury, vaccinations, and certain oral medications such as steroids. Subsequently, the immune system is thought to induce inflammation and excessive skin cell reproduction, which can be exacerbated by additional factors such as stress and diet.

The goal of current treatments has been to decrease the severity and extent of psoriasis to the point at which it no longer interferes substantially with the patient's occupation, well-being, or personal or social life. The initial treatment for stable plaque psoriasis of any severity is topical. In patients in which more than 20 percent of the skin is affected, however, topical treatment alone may be impractical and systemic therapy may also be indicated at the outset.

The topical treatment for plaque psoriasis incorporates the use of emollients, keratolytic agents, coal tar, anthralin, corticosteroids of medium to strong potency, and calpotriene. All of these treatments have variable efficacy, fail to prevent frequent relapses of the disease, exhibit side effects, and pose cosmetic problems of their own. The use of steroids may also lead to resistance, rendering subsequent steroid treatment ineffective.

Systemic treatment has been used in patients with physically, socially, or economically disabling psoriasis that has not responded to topical treatment. The choices to date have been phototherapy or systemic drug therapy. Generally, systemic treatment has employed phototherapy with Ultraviolet B irradiation, photo chemotherapy which combines the photosensitizing drug methoxsalen with Ultraviolet A phototherapy (PUVA), methotrexate, etretinate, systemic corticosteroids, and cyclosporine. Each of these systemic treatments has variable efficacy and undesired side effects, and some of them are very toxic and present frequent relapses of the disease. For example, long term use of phototherapies may prematurely age the skin and increase the incidence of skin cancers. The use of methotrexate requires careful monitoring to avoid liver damage. Use of oral retinoids must be carefully controlled in women because of the potential for severe birth defects. This risk extends for years after the use of the drug has been terminated. Cyclosporine, an immunosuppresant, is reserved for patients that have failed other internal treatments, or for whom the other internal treatments are contraindicated. Rotating between therapies, and combinations of topical medications with phototherapies, have also been found to be useful regimens in the treatment of psoriasis.

Accordingly, there is at present an urgent need for an effective psoriasis treatment that avoids the disadvantages associated with the currently available topical or systemic treatments, with improved efficacy, safety, and side effect profiles.

It is an object of the present invention to provide an effective treatment of psoriasis, showing clinical benefit.

In particular, it is an object of the invention to provide dosages and schedules of compounds that can be used for psoriasis therapy in humans, avoiding toxicities while maintaining the desired effects.

It is yet another object of the invention to provide new products, for administration in the treatment of psoriasis.

SUMMARY OF THE INVENTION

We have developed a method to treat a mammal suffering from skin disease with kahalalide compounds, in particular kahalalide F, avoiding toxicity and leading to clinical improvement.

The kahalalide compounds are peptides isolated from a Hawaiian herbivorous marine species of mollusc, *Elysia rufescens*. Kahalalides A-F are described in EP 610 078 and Hamman et al., J. Am. Chem. Soc., 1993, 115, 5825-5826.

Kahalalide A-G are described in Hamann, M. et al., J. Org. Chem, 1996, 61, 6594-6600: "Kahalalides: bioactive peptides from a marine mollusk *Elysia rufescens* and its algal diet *Bryopsis* sp.".

Kahalalide H and J are described in Scheuer P. J. et al., J. Nat. Prod. 1997, 60, 562-567: "Two acyclic kahalalides from the sacoglossan mollusk *Elysia rufescens*".

Kahalalide O is described in Scheuer P. J. et al., J. Nat. Prod. 2000, 63(1) 152-4: A new depsipeptide from the sacoglossan mollusk *Elysia ornata* and the green alga Bryopsis species".

For kahalalide K, see Kan, Y. et al., J. Nat. Prod. 1999 62(8) 1169-72: "Kahalalide K: A new cyclic depsipeptide from the hawaiian green alga *bryopsis* species".

For related reports, see also Goetz et al., Tetrahedron, 1999, 55; 7739-7746: "The absolute stereochemistry of Kahalalide F"; Albericio, F. et al. Tetrahedron Letters, 2000, 41, 9765-9769: "Kahalalide B. Synthesis of a natural cyclodepsipeptide"; Becerro et al. J. Chem. Ecol. 2001, 27(11), 2287-99: "Chemical defenses of the sarcoglossan mollusk *Elysia rufescens* and its host Alga *bryopsis* sp.".

The synthesis and cytotoxic activities of natural and synthetic kahalalide compounds is described in WO 01 58934.

Of the kahalalide compounds, kahalalide F is the most promising because of its antitumoural activity. Kahalalide F is reported in EP 610 078 to have the structure:

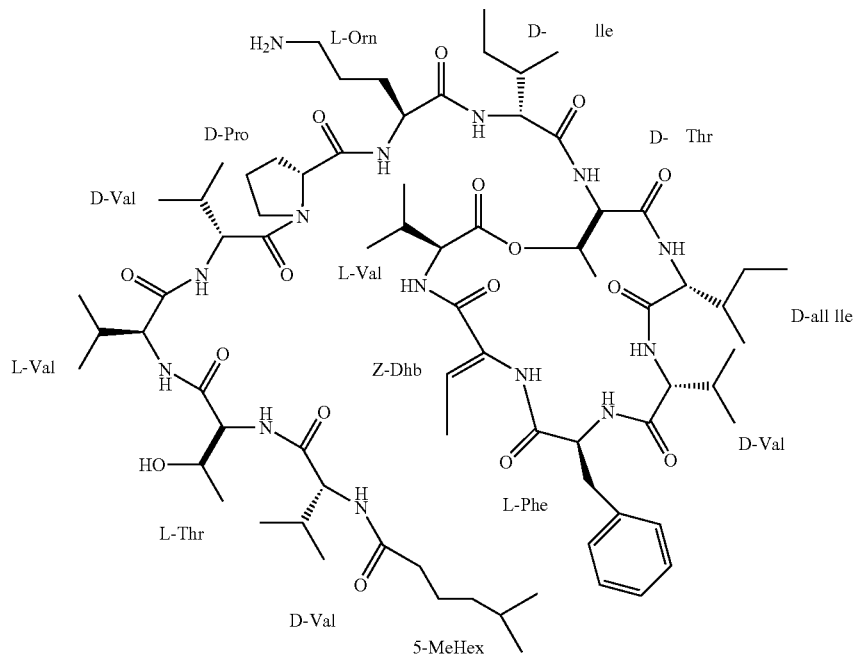

Kahalalide F is a tridecapeptide with a ring shape side and a lateral side, containing a fatty acid group connected to the latter. Its activity against in vitro cell cultures of human lung carcinoma A-549 and human colon carcinoma HT-29 were reported in EP 610 078.

WO 02 36145 describes pharmaceutical compositions containing kahalalide F and new uses of this compound in cancer therapy.

See also Beijnen, J. H. et al., Drug Dev. Ind. Pharm. 2001, 27(8) 767-80: "Development of a lyophilized parenteral pharmaceutical formulation of the investigational polypeptide marine anticancer agent kahalalide F"; Beijnen, J. H. et al., Br. J. Clin. Pharmacol. 2002, 53(5), 543: "Bioanalysis of the novel peptide anticancer drug kahalalide F in human plasma by h.p.l.c. under basic conditions coupled with positive turbo-ionspray tandem mass spectrometry"; Beijnen, J. H. et al., PDA J. Pharm. Sci. Technol. 2001, 55(4) 223-9: "In vitro hemolysis and buffer capacity studies with the novel marine anticancer agent Kahalalide F and its reconstitution vehicle cremophor EL/ethanol"; Sparidans R. W. et al., Anticancer Drugs 2001, 12(7) 575-82: "Chemical and enzymatic stability of a cyclic depsipeptide, the novel, marine-derived, anti-cancer agent kahalalide F".

In preclinical studies, kahalalide F has shown significant activity against solid tumour cell lines, and selectivity for, but not restricted to, prostate tumour cells, neuroblastomas, some primary sarcoma lines and tumour cells that overexpress the Her2/neu oncogene. In vitro exposure studies demonstrated that kahalalide F is not schedule dependent. Its mechanism of action is not yet elucidated, in vitro studies have shown activity of kahalalide F to cause cell swelling and ultimately death, see for example Garcia-Rocha M, Bonay P, Avila J., Cancer Lett. 1996 99(1) 43-50: "The antitumoural compound Kahalalide F acts on cell lysosomes".

Preclinical in vivo studies determined that the maximum tolerated dose (MTD) of KF in female mice following a single bolus iv injection was to be 280 µg/kg. Whereas single doses just above the MTDiv were extremely toxic, with animals exhibiting signs of neurotoxicity followed by death, 280 µg/kg KF could be administered repeatedly, according to a once daily times five schedule, without any apparent evidence of acute toxicity. See Supko, F. et al., Proceedings of the 1999 AACR NCI EORTC International Conference, abstract 315: "Preclinical pharmacology studies with the marine natural product Kahalalide F".

In our application PCT/GB2002/004735, incorporated herein by reference in its entirety, guidance is given for the treatment of humans with kahalalide compounds, in particular kahalalide F, in a clinical setting. Dosages and schedules are described there, as well as procedures to limit the toxicities that can be caused by these compounds.

Unexpectedly, in the course of a clinical trial for the treatment of cancer we have found that kahalalide compounds, and in particular kahalalide F, are effective in the treatment of psoriasis.

DETAILED DESCRIPTION

The present invention is thus directed to a method of treating a skin disease involving hyperproliferation of dermis cells in a mammal which comprises administering to the mammal an effective, non-toxic amount of a kahalalide compound, preferably kahalalide F. The skin disease is preferably psoriasis.

In one aspect the present invention provides a method for treating a human patient afflicted with psoriasis, comprising administering to said patient a therapeutically effective amount of a kahalalide compound, or a pharmaceutical composition thereof. More preferably the kahalalide compound is kahalalide F.

The present invention can be employed particularly for treatment of patients with refractory psoriasis that do not respond favourably to other treatments. In particular, the compositions of this invention can be employed after other therapy has been tried and not worked.

In another aspect, the present invention provides a method for treating a human patient afflicted with psoriasis, comprising administering to said patient a kahalalide compound at a dose below 1200 mcg/m2/day, preferably below 930 mcg/m2/day and more preferably below 800 mcg/m2/day. Suitably the dose is at least 320 mcg/m2/day. Preferably the dose is in the range of 400-900 mcg/m2/day, preferably 500-800 mcg/m2/day, more preferably 600-750 mcg/m2/day. Especially preferred are doses of about 650-700 mcg/m2/day, in particular about 650 mcg/m2/day. The above dosages allow for an effective psoriasis therapy in humans.

In a further aspect the kahalalide compound is administered intravenously. Preferably in cycles of 1-4 weeks. A weekly cycle is most preferred. Infusion time is preferably from about 1 to about 24 hours, more preferably from about 1 hour to about 3 hours. Especially preferred is an infusion time of about 1 hour.

The present invention provides a pharmaceutical composition containing a recommended dose of a kahalalide compound for the treatment of psoriasis and a pharmaceutically acceptable carrier. Preferably the pharmaceutical composition is for a treatment selected from intravenous infusion, intradermal infusion or topical. Preferably an intravenous infusion is used.

In a further aspect of the present invention, a medical kit for administering a kahalalide compound is provided, comprising printed instructions for administering the kahalalide compound according to the doses and schedules set forth above, and a supply of kahalalide compound in dosage units for at least one cycle, wherein each dosage unit contains the appropriate amount of kahalalide compound for the treatments as defined above and a pharmaceutically acceptable carrier.

The invention further provides for the use of kahalalide compounds in the manufacture of a medicament for the procedures and methods of this invention.

The term "kahalalide compound" includes natural compounds, their mixtures and new compounds, for example as defined in WO 01 58934 which is incorporated herein in its entirety by reference. Especially preferred is the compound kahalalide F.

Thus, the present invention employs a natural kahalalide such as kahalalide F or a mimic of a natural kahalalide. The mimic compounds may differ in one or more amino acids, and one or more components of the acyl side chain. Preferably they differ in one or more components of the acyl side chain. Examples of the kahalalide compound for use in this invention particularly include the compound identified as kahalalide F with a 5-methylhexyl side chain, and compounds differing only in the side chain such as the 4-methylhexyl analogue, especially the 4-(S)-methylhexyl analogue, and mixtures thereof.

More especially, the kahalalide can be kahalalide F prepared in accordance with the teachings of EP 610 078, more especially kahalalide F fitting the data given in EP 610 078; a kahalalide having the structure shown for kahalalide F in EP 610 078 with the 5-methylhexyl sidechain and prepared by synthetic or other means; or a kahalalide having the structure shown in EP 610 078 but with a 4-methylhexyl sidechain, especially a 4-(S)-methylhexyl sidechain.

Suitably the mimics have at least one of the following features to differentiate from a parent naturally occurring kahalalide:

1 to 7, especially 1 to 3, more especially 1 or 2, most especially 1, amino acid which is not the same as an amino acid of the parent compound;

1 to 10, especially 1 to 6, more especially 1 to 3, most especially 1 or 2, additional methylene groups in the side chain acyl group of the parent compound;

1 to 10, especially 1 to 6, more especially 1 to 3, most especially 1 or 2, methylene groups omitted from the side chain acyl group of the parent compound;

1 to 6, especially 1 to 3, more especially 1 or 3, substituents added to or omitted from the side chain acyl group of the parent compound.

For cyclic kahalalides, the amino acid addition or omission can be in the cyclic ring or in the side chain.

Examples of mimic compounds are compounds related to kahalalide F, and having the formula:

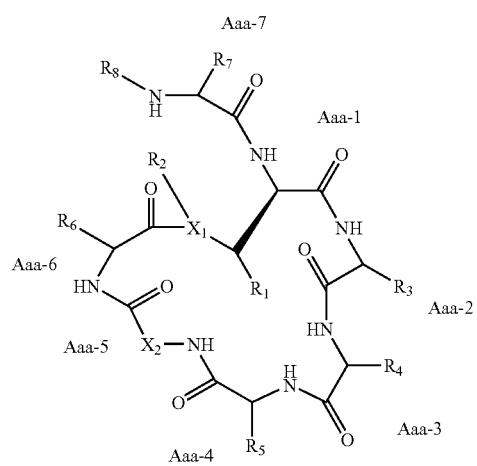

Formula II wherein $Aaa_1$, $Aaa_2$, $Aaa_3$, $Aaa_4$, $Aaa_6$, and $Aaa_7$ are independently α-amino acids of L or D configuration, if applies; wherein $R_1$, $R_2$, $R_3$, $R_4$, $R_5$, $R_6$, $R_7$ are each independently H or an organic group selected from the group consisting of an alkyl group, an aryl group, an aralkyl group, and their substituted derivatives with an hydroxy group, a mercapto group, an amino group, a guanidino group, a halogen group; wherein $X_1$ is independently O, S, or N; wherein $R_2$ is, if applies, independently H or an organic group selected from the group consisting of an alkyl group and an aralkyl group; wherein $Aaa_5$ is independently an amino acid of L or D configuration, if applies; wherein $X_2$ is independently an organic group selected from the group consisting of an alkenyl, an alkyl group, an aryl group, an aralkyl group, and their substituted derivatives with an hydroxy group, a mercapto independently H or an organic group selected from the group consisting of an alkyl group, an aryl group, an aralkyl group, and their substituted derivatives with an hydroxy group, a mercapto group, an amino group, a guanidino group, a halogen group; wherein $R_8$ is independently of the following formulae III, IV, or V:

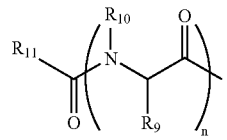

Formula III

-continued

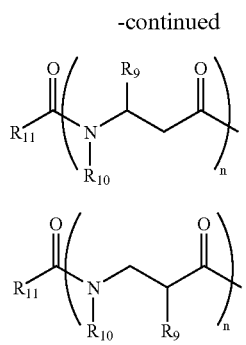

Formula IV

Formula V wherein $R_9$, $R_{10}$, and $R_{11}$ are each independently H or an organic group selected from the group consisting of an alkyl group, an aryl group, an aralkyl group, and their substituted derivatives with an hydroxy group, a mercapto group, an amino group, a guanidino group, a carboxyl group, a carboxamido group, a halogen group; $R_9$ and $R_{10}$ can form part of the same cycle; $R_9$ can confer S or R configuration, if applies, to the carbon attached to; and n is 0 to 6. The definitions of the amino acids can also be varied to allow for proline and analogous amino acids including hydroxyproline. The formulae (III), (IV) and M can be intermixed to give a side chain made up of repeat units in more than one of these formulae.

In a modification, one or more of the ring amino acids Aaa-6 and Aaa-5 of the hexamino acid cycle is omitted or an amino acid Aaa-7 is added between Aaa-6 and Aaa-1, in order to arrive at rings having four, five or seven ring amino acids. Six ring amino acids is preferred.

Administration of the compounds or compositions of the present invention can be parenteral or topical, preferably it is by intravenous infusion. Infusion times of up to 72 hours can be used, more preferably 1 to 24 hours, with either about 1 or about 3 hours most preferred. Short infusion times which allow treatment to be carried out without an overnight stay in hospital are especially desirable. However, infusion may be around 24 hours or even longer if required.

Although guidance for the dosage is given above, the correct dosage of the compound will vary according to the particular formulation, the mode of application, and the particular psoriasis being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The administration is performed in cycles, in the preferred application method, an intravenous infusion of kahalalide compounds given to the patients the first week of each cycle, the patients are allowed to recover for the remainder of the cycle. The preferred duration of each cycle is of either 1, 3 or 4 weeks; multiple cycles can be given as needed. Dose delays and/or dose reductions and schedule adjustments are performed as needed depending on individual patient tolerance of treatments, in particular dose reductions are recommended for patients with higher than normal serum levels of liver transaminases or alkaline phosphatase.

Pharmaceutical compositions of kahalalide compounds that can be used include liquid (solutions, suspensions or emulsions) with suitable composition for intravenous administration, and they may contain the pure compound or in combination with any carrier or other pharmacologically active compounds. Further guidance concerning the pharmaceutical compositions can be found in WO 02 36145 which is incorporated herein by reference in its entirety. Topical and intradermal formulations of kahalalide compounds, in particular kahalalide F are also contemplated within the scope of the invention.

A combination of a non-ionic surfactant and an organic acid is suited for use with a bulking agent to give a lyophilised form of a kahalalide compound suited for reconstitution. Reconstitution is preferably effected with a mix of emulsifying solubiliser, alkanol and water.

The lyophilised composition preferably comprises mainly the bulking agent, such as at least 90% or at least 95% bulling agent. Examples of bulking agents are well known and include sucrose and mannitol. Other bulking agents can be employed.

The non-ionic surfactant in the lyophilised composition is preferably a sorbitan ester, more preferably a polyethylene sorbitan ester, such as a polyoxyethylene sorbitan alkanoate, especially a polyoxyethylene sorbitan mono-oleate, for example polysorbate 80. The non-ionic surfactant typically comprises a few % of the composition, such as 0 to 5% of the composition, for instance 2 to 3 or 4% of the composition.

The organic acid in the lyophilised composition is typically an aliphatic acid, preferably a hydroxycarboxylic acid and more preferably a hydroxypolycarboxylic acid, notably citric acid. The organic acid typically comprises a few % of the composition, such as 0 to 5% of the composition, for instance 2 to 3 or 4% of the composition.

The amount of kahalalide compound in the lyophilised composition is typically less than 3%, or often less than 2.5%, of the mix.

The emulsifying solubiliser for the reconstituting agent suitably comprises an polyethylene glycol ester, notably an ester of a fatty acid, more preferably a PEG oleate such as PEG-35 oleate. The emulsifying solubiliser is suitably 0 to 25% of the reconstituting agent, typically about 5 to 20%, say about 15%. The alkanol is usually ethanol, and is suitably 0 to 25% of the reconstituting agent, typically about 5 to 20%, say about 15%. The remainder of the reconstituting agent is water, and gives a reconstituted solution suited for intravenous injection.

Further dilution of the reconstituted solution with 0.9% saline may be appropriate for infusion of the kahalalide compound.

In a particularly preferred embodiment, the lyophilised composition comprises 1 mg kahalalide F; 50 mg sucrose; 1 mg anhydrous citiric acid; and 1 mg of polysorbate 80.

The preferred reconstituting agent then comprises 5 to 20%, say about 15%, emulsifying solubiliser; 5 to 20%, say about 15%, alcohol; and remainder water.

The invention additionally provides kits comprising separate containers containing the lyophilised composition and the reconstituting agent. Methods of reconstitution are also provided.

The present invention further provides a method of treating any mammal, notably a human, affected by psoriasis which comprises administering to the affected individual a therapeutically effective amount of a pharmaceutical composition thereof prepared by reconstitution of a lyophilised composition of this invention.

In one embodiment, the reconstituted solution is prepared for infusion and is administered in a 1-3 hour infusion on concentrations of up to around 20 or 25 µg/ml, typically up to 15 µg/ml. Suitable infusion equipment preferably includes a glass container, rather than one of polyethylene. Tubing is preferably of silicone.

We prefer that infusion times of up to 24 hours are used, and as explained we prefer an infusion time of about 1 hour. In a variation, the infusion time is 2-12 hours, such as 2-6 hours. Short infusion times which allow treatment to be carried out without an overnight stay in hospital are especially desirable. However, infusion may be 12 to 24 hours or even longer if required. Infusion may be carried out at suitable intervals of say 2 to 4 weeks. In an alternative dosing protocol, the kahalalide compound such as kahalalide F is administered for say about 1 hour for 5 consecutive days every 3 weeks. Other protocols can be devised as variations.

The compounds and compositions of this invention may be used with other drugs or therapy to provide a combination therapy. The other drugs may form part of the same composition, or be provided as a separate composition for administration at the same time or a different time. The identity of the other drug is not particularly limited, and reference is made among others to those mentioned above.

EXAMPLES OF THE INVENTION

A patient with a neck and head cancer being in a clinical trial with kahalalide F administration by weekly infusion (KHF A-002-01) entered at the dose level that nowadays is the recommended dose for the further studies (650 µg/m$^2$). This phase I Clinical and Pharmacokinetic study was designed to determine the safety of Kahalalide F administered as a weekly infusion over 1 hour in patients with solid tumours. This trial was addressed to any solid tumours and was designed as a classical escalation. The patient was a 60 years patient with a psoriasis history since more than 40 years. At the moment of the KHF treatment started, he showed a severe grade psoriasis. After the first KHF infusion, the patient experimented a quick improvement of the psoriasic symptoms, followed by an important remission of the cutaneous plaques. With the following KHF infusions there was an important clinical improvement of his severe psoriasis, reaching a nearly complete remission of the cutaneous plaques. This patient received a total of 7 KHF infusions before progress of his neck and head tumour. However, two months after the last KHF dose administration, the patient severe psoriasis was still in a nearly complete remission situation.

The invention claimed is:

1. A method for treating psoriasis in a mammal which comprises administering to the mammal an effective, non-toxic amount of a kahalalide compound.

2. The method according to claim 1, wherein the mammal is a human patient.

3. The method according to any of claims 1 or 2, wherein the kahalalide compound is kahalalide F, 4-methylhexyl analogue or a mixture thereof.

4. The method according to claim 3, wherein the kahalalide compound is kahalalide F.

5. The method according to claim 1 or 2, wherein the kahalalide compound is used in combination with other drug or drugs or therapy to provide a combination therapy.

6. The method according to claim 4, wherein the kahalalide compound is administered at a dose level between 1200 µg/m$^2$/day and 320 µg/m$^2$/day.

7. The method according to claim 6, wherein the dose level is between 800 µg/m$^2$/day and 500 µg/m$^2$/day.

8. The method according to claim 7, wherein the dose level is 650 µg/m$^2$/day.

9. The method according to claim 4, wherein the kahalalide compound is administered intravenously in cycles of 1-4 weeks.

10. The method according to claim 9, wherein the kahalalide compound is administered in a weekly cycle.

* * * * *